US009999805B2

(12) United States Patent
Ahuja et al.

(10) Patent No.: US 9,999,805 B2
(45) Date of Patent: Jun. 19, 2018

(54) ANALYZING TEAM GAME PLAY INTERACTIONS USING GAZE DATA (71) Applicant: International Business Machines Corporation, Armonk, NY (US)

(72) Inventors: Karan Ahuja, New Delhi (IN); Kuntal Dey, New Delhi (IN); Seema Nagar, Bangalore (IN); Roman Vaculin, Bronxville, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 12 days.

(21) Appl. No.: 15/184,248

(22) Filed: Jun. 16, 2016

(65) Prior Publication Data

US 2017/0361158 A1  Dec. 21, 2017

(51) Int. Cl.
*A63F 13/213* (2014.01)
*A63B 24/00* (2006.01)
*A63B 71/06* (2006.01)

(52) U.S. Cl.
CPC .......... *A63B 24/0062* (2013.01); *A63B 71/06* (2013.01); *A63F 2300/1087* (2013.01)

(58) Field of Classification Search
None
See application file for complete search history.

(56) References Cited

U.S. PATENT DOCUMENTS

| 8,696,126 | B2 | 4/2014 | Yoo et al. | |
| 2010/0283630 | A1 | 11/2010 | Alonso | |
| 2011/0007275 | A1* | 1/2011 | Yoo | A61B 3/113 351/209 |
| 2012/0092618 | A1 | 4/2012 | Yoo et al. | |
| 2013/0095924 | A1* | 4/2013 | Geisner | G06F 3/012 463/32 |

(Continued)

OTHER PUBLICATIONS

Ahuja et al., "Analyzing and Interpreting a Referee's Actions Using Gaze Data," U.S. Appl. No. 15/184,239, filed Jun. 16, 2016.

(Continued)

*Primary Examiner* — Jason Yen
(74) *Attorney, Agent, or Firm* — Cantor Colburn LLP (57) ABSTRACT

Systems, methods, and computer-readable media are disclosed for capturing, over the course of a sports match, gaze data for each participant on a team, identifying a team-level key performance indicator (KPI) associated with a sports domain to which the sports match corresponds, and generating KPI data corresponding to the KPI. A graph may then be constructed based at least in part on the KPI data, where each node in the graph may represent a player on the team or an object of interest, and each edge connecting adjacent nodes may be weighted to indicate a degree of interaction between the nodes connected by the edge. KPI data may be aggregated across multiple sports domain KPIs and analyzed to assess team performance characteristics during the sports match. Report data indicative of team performance for different game scenarios, and optionally including recommendations for improving team performance in such scenarios, may be generated.

20 Claims, 6 Drawing Sheets (56) References Cited

U.S. PATENT DOCUMENTS

| | | | |
|---|---|---|---|
| 2013/0293844 A1* | 11/2013 | Gross | A61B 3/0025 |
| | | | 351/209 |
| 2014/0111630 A1 | 4/2014 | Pires et al. | |
| 2014/0184550 A1* | 7/2014 | Hennessey | G06F 3/013 |
| | | | 345/173 |
| 2015/0220779 A1 | 8/2015 | Publicover et al. | |
| 2015/0256674 A1* | 9/2015 | Iwasaki | G06F 3/013 |
| | | | 455/414.1 |
| 2016/0078119 A1* | 3/2016 | Aravkin | G06F 17/30598 |
| | | | 707/738 |
| 2016/0328130 A1* | 11/2016 | Patel | G06F 3/013 |
| 2017/0169658 A1* | 6/2017 | Froy | G07F 17/3225 |

OTHER PUBLICATIONS

Ahuja et al., "Determining Player Peformance Statistics Using Gaze Data," U.S. Appl. No. 15/184,229, filed Jun. 16, 2016.
List of IBM Patents or Patent Applications Treated as Related; (Appendix P), Filed Jun. 17, 2016, 2 pages.
Undisclosed: "Teaching Baseball Professionals With Mobile Eye Tracking," (M2 Presswire via Comtex), Feb. 23, 2011, 1 page.
Vickers, J N; Ttl: Advances in coupling perception and action: the quiet eye as a bidirectional link between gaze, attention and action; Publication Ttl: Mind and Motion: The Bidirectional Link Between Thought and Action, vol. 174, pp. 279-288; 2009.

* cited by examiner

ANALYZING TEAM GAME PLAY INTERACTIONS USING GAZE DATA

BACKGROUND

This application is related to co-pending application entitled "Determining Player Performance Statistics Using Gaze Data," having Ser. No. 15/184,229, and to co-pending application entitled "Analyzing and Interpreting a Referee's Actions Using Gaze Data," having Ser. No. 15/184,239.

BACKGROUND

Participants in a sports match (also referred to as a game, contest, or the like) may have different skill levels that may impact their performance in response to different situations that may arise during the match. Parameters that may impact a sports participant's skill level may include, for example, reaction time, response time, attentiveness, hand-eye coordination, and so forth. These parameters may vary across sports participants, and may also vary for a given sports participant throughout a match depending on the particular situation that the participant encounters. For example, a left-handed baseball player may exhibit a faster reaction and response time when batting against a left-handed pitcher as opposed to a right-handed pitcher. In addition, a sports participant's response to a particular situation may vary over time throughout the match. For example, a tennis player's attentiveness may vary over time causing certain backhand returns to be struck with greater accuracy than other backhand returns.

In team sports, the members of a team may exhibit varying levels of skill. Further, a team member's skill level may be particularly suited for a particular position or role the team member has on the team. An individual sports participant is generally unaware during a sporting match of how his performance statistically differs for different scenarios that may arise during the match. Further, an individual participant is also generally unaware of how her performance impacts the performance of other team members, whether her performance is consistent with her responsibilities on the team for a given game situation, whether her performance is consistent with team goals (e.g., a desired team arrangement/formation for a given situation), and so forth. While there exist certain match analysis tools for assessing team dynamics during a sports match (e.g., reviewing match footage), such tools fail to elucidate granular differences in performance characteristics among team members over the course of the match for the multitude of match scenarios that may occur. Such tools also fail to provide an accurate assessment of an attentiveness level of each team member and the degree to which deviations from expected levels of attentiveness or other expected performance characteristics impacts team performance. Discussed herein are technical solutions that address at least some of the aforementioned drawbacks as well as other drawbacks.

SUMMARY

In one or more example embodiments of the disclosure, a computer-implemented method for analyzing interactions between members of a team using gaze parameter data is disclosed. The method includes capturing, by an image sensor over a period of time during a sports match, the gaze parameter data, where the gaze parameter data includes first gaze parameter data associated with a first member of the team and second gaze parameter data associated with second member of the team. The method further includes identifying, by a computer processor, a sports domain associated with the sports match, and identifying, by the computer processor, a key performance indicator (KPI) corresponding to the sports domain. The method additionally includes identifying, by the computer processor, one or more sports domain rules associated with the KPI, and filtering, by the computer processor, the gaze parameter data to obtain a location/time series of the gaze parameter data that satisfies the one or more sports domain rules. The method further includes generating, by the computer processor, KPI data associated with the KPI based at least in part on the location/time series of the gaze parameter data, and analyzing, by the computer processor, the KPI data to determine a mutual gazing behavior between the first member of the team and the second member of the team.

In one or more other example embodiments of the disclosure, a system for determining player performance statistics using gaze parameter data is disclosed that includes at least one memory storing computer-executable instructions; and at least one processor configured to access the at least one memory and execute the computer-executable instructions to capture, by an image sensor over a period of time during a sports match, the gaze parameter data, where the gaze parameter data includes first gaze parameter data associated with a first member of the team and second gaze parameter data associated with second member of the team. The at least one processor is further configured to identify a sports domain associated with the sports match, and identify a key performance indicator (KPI) corresponding to the sports domain. The at least one processor is further configured to identify one or more sports domain rules associated with the KPI, and filter the gaze parameter data to obtain a location/time series of the gaze parameter data that satisfies the one or more sports domain rules. The at least one processor is further configured to generate KPI data associated with the KPI based at least in part on the location/time series of the gaze parameter data, and analyze the KPI data to determine a mutual gazing behavior between the first member of the team and the second member of the team.

In one or more other example embodiments of the disclosure, a computer program product for analyzing interactions between members of a team using gaze parameter data is disclosed that comprises a non-transitory storage medium readable by a processing circuit, the storage medium storing instructions executable by the processing circuit to cause a method to be performed. The method includes obtaining the gaze parameter data, where the gaze parameter data is captured by an image sensor over a period of time during a sports match, and where the gaze parameter data includes first gaze parameter data associated with a first member of the team and second gaze parameter data associated with second member of the team. The method further includes identifying, by a computer processor, a sports domain associated with the sports match, and identifying, by the computer processor, a key performance indicator (KPI) corresponding to the sports domain. The method additionally includes identifying, by the computer processor, one or more sports domain rules associated with the KPI, and filtering, by the computer processor, the gaze parameter data to obtain a location/time series of the gaze parameter data that satisfies the one or more sports domain rules. The method further includes generating, by the computer processor, KPI data associated with the KPI based at least in part on the location/time series of the gaze parameter data, and analyzing, by the computer processor, the KPI data to determine a mutual gazing behavior between the first member of the team and the second member of the team.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral identifies the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Example embodiments of the disclosure include, among other things, systems, methods, computer-readable media, techniques, and methodologies for capturing, over the course of a sports match, gaze data for each participant on a team, identifying a team-level key performance indicator (KPI) associated with a sports domain to which the sports match corresponds, and generating KPI data corresponding to the KPI. A graph may then be constructed based at least in part on the KPI data, where each node in the graph may represent a player on the team or an object of interest, and each edge connecting adjacent nodes may be weighted to indicate a degree of interaction between the nodes connected by the edge. For any given player, an object of interest may be an object that is being transferred between players as part of the sports match (e.g., a ball, puck, etc.) or another player.

In certain example embodiments, KPI data may be aggregated across multiple sports domain KPIs and analyzed to assess team performance characteristics during the sports match. Report data indicative of team performance for different game scenarios may be generated and presented to team members and/or other decision makers (e.g., a coach). The report data may further include recommendations for improving team performance in different scenarios.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
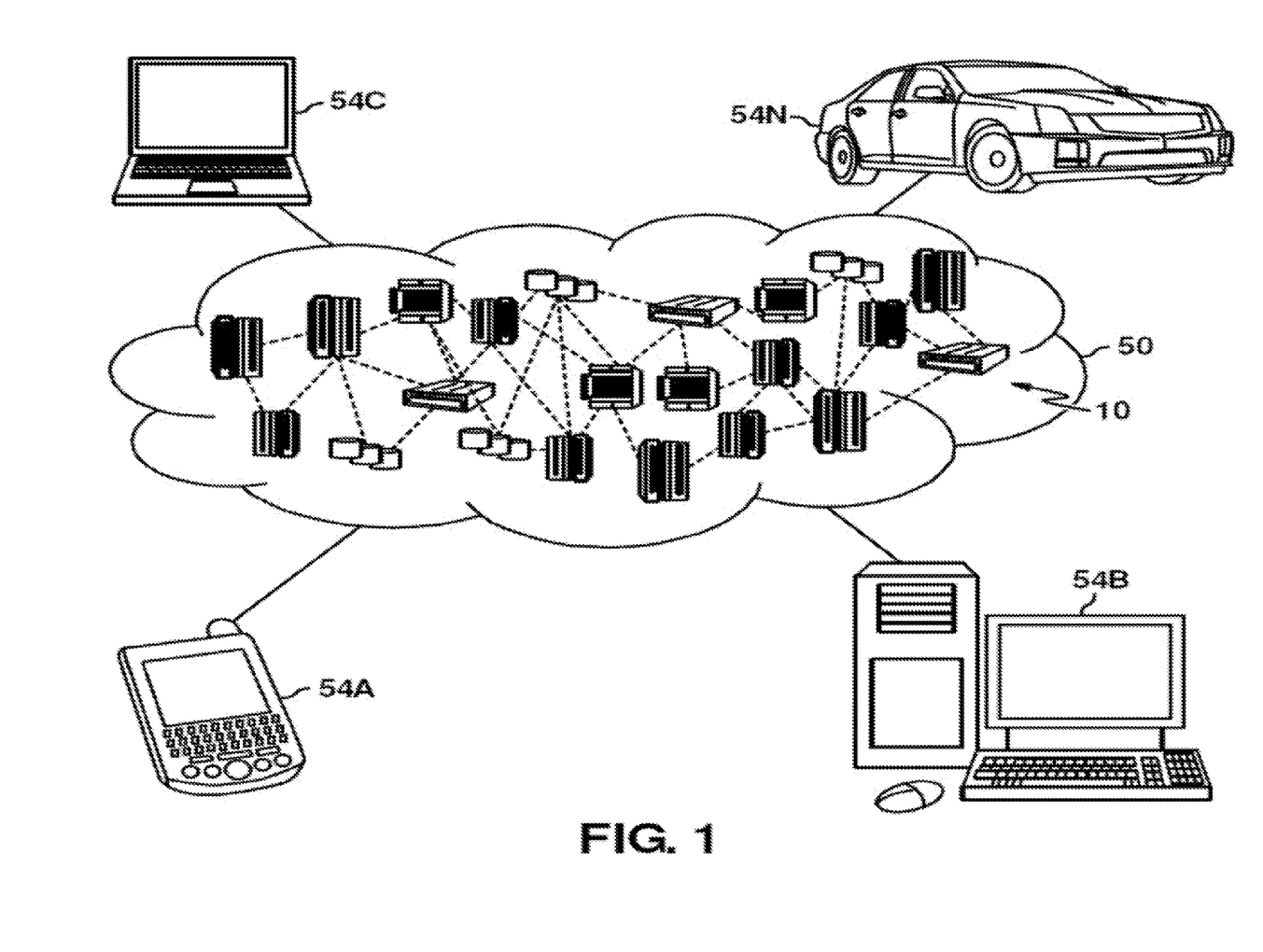
FIG. 1 depicts a cloud computing environment in accordance with one or more example embodiments of the disclosure.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
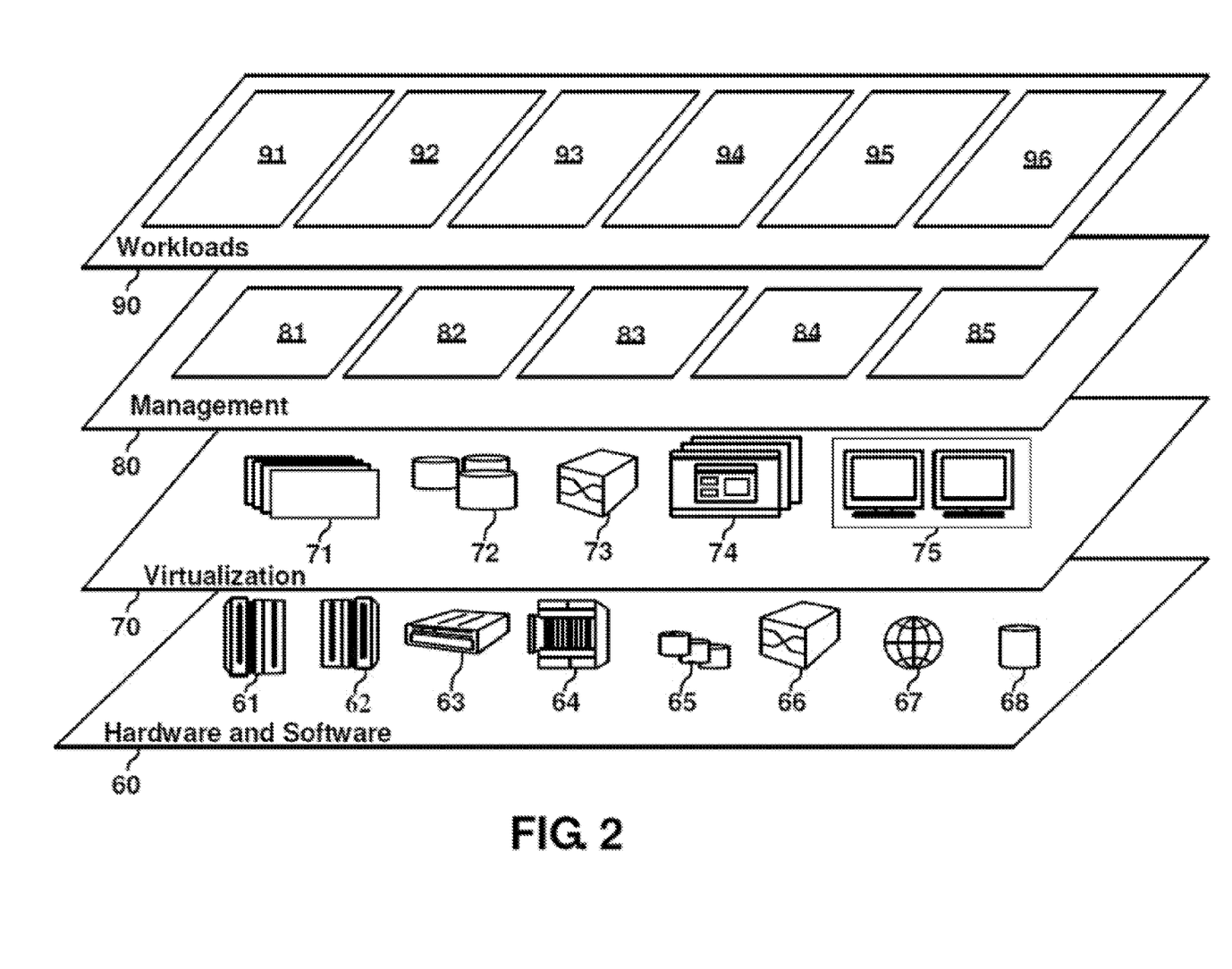
FIG. 2 depicts abstraction model layers in accordance with one or more example embodiments of the disclosure.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and photograph sharing 96.

Figure 3:
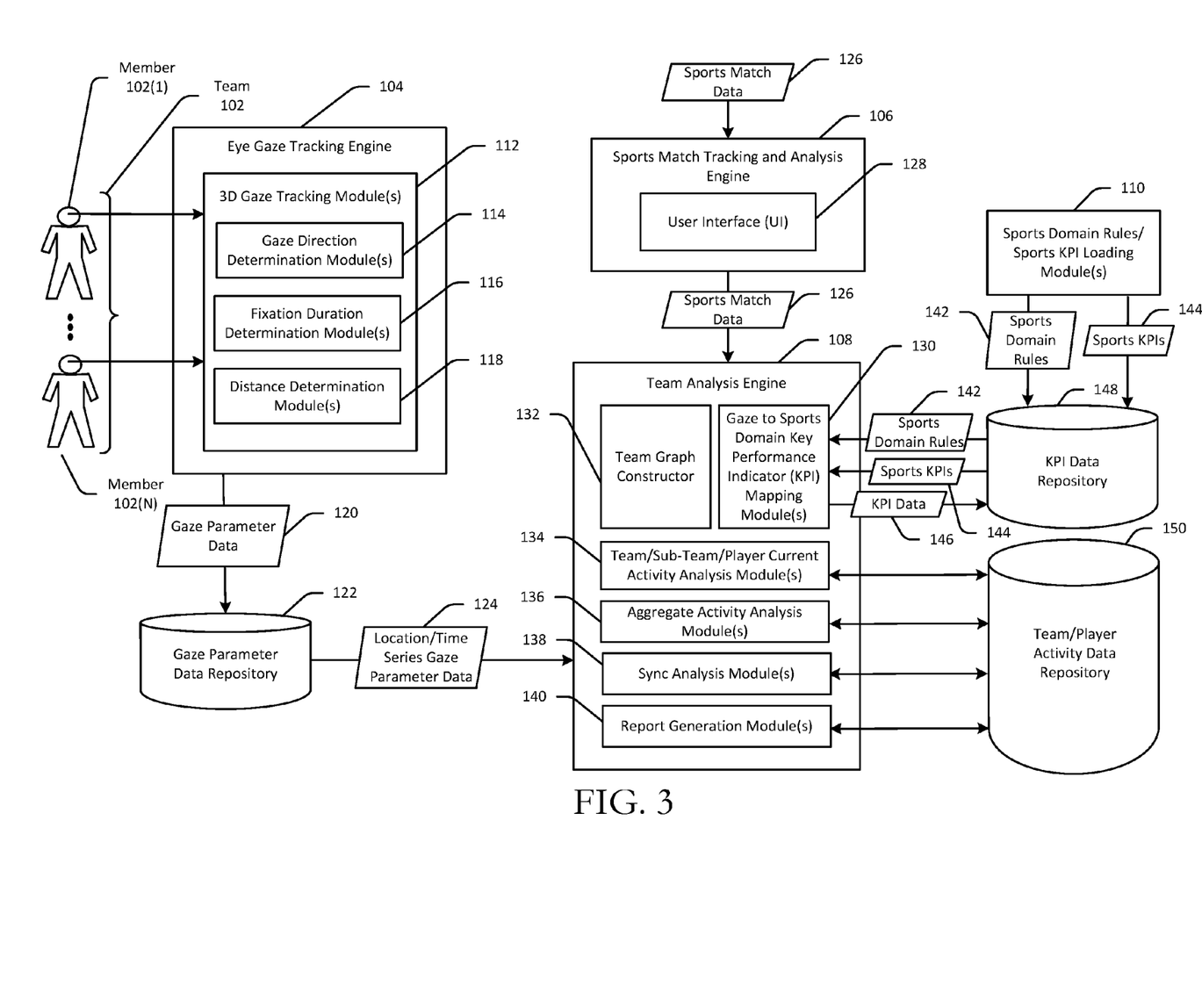
FIG. 3 is a schematic block diagram depicting illustrative components of a three-dimensional (3D) gaze-based team analysis system in accordance with one or more example embodiments of the disclosure.
Figure 4:
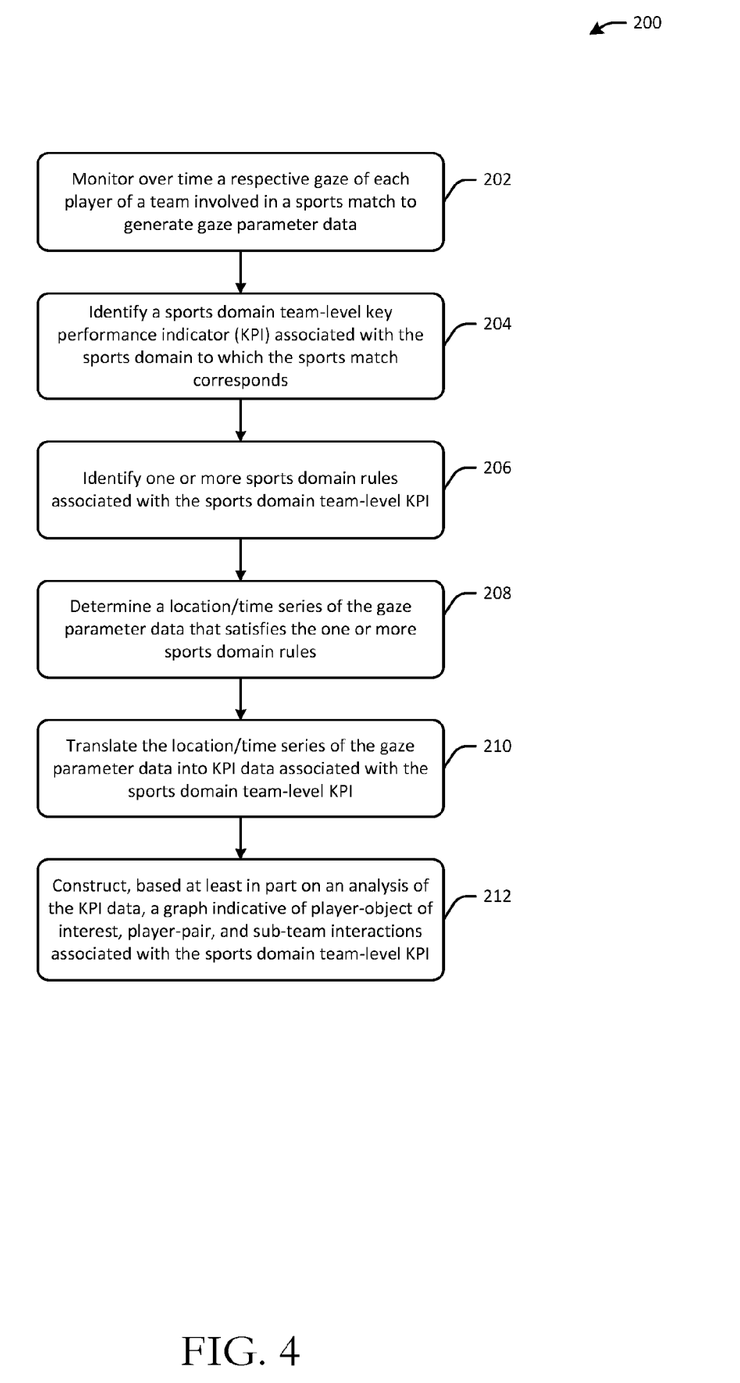
FIG. 4 is a process flow diagram of a method for generating key performance indicator (KPI) data associated with a sports domain KPI based at least in part on gaze parameter data and generating a graph based at least in part on the KPI data indicative of various interactions between team members in accordance with one or more example embodiments of the disclosure.
Figure 5:
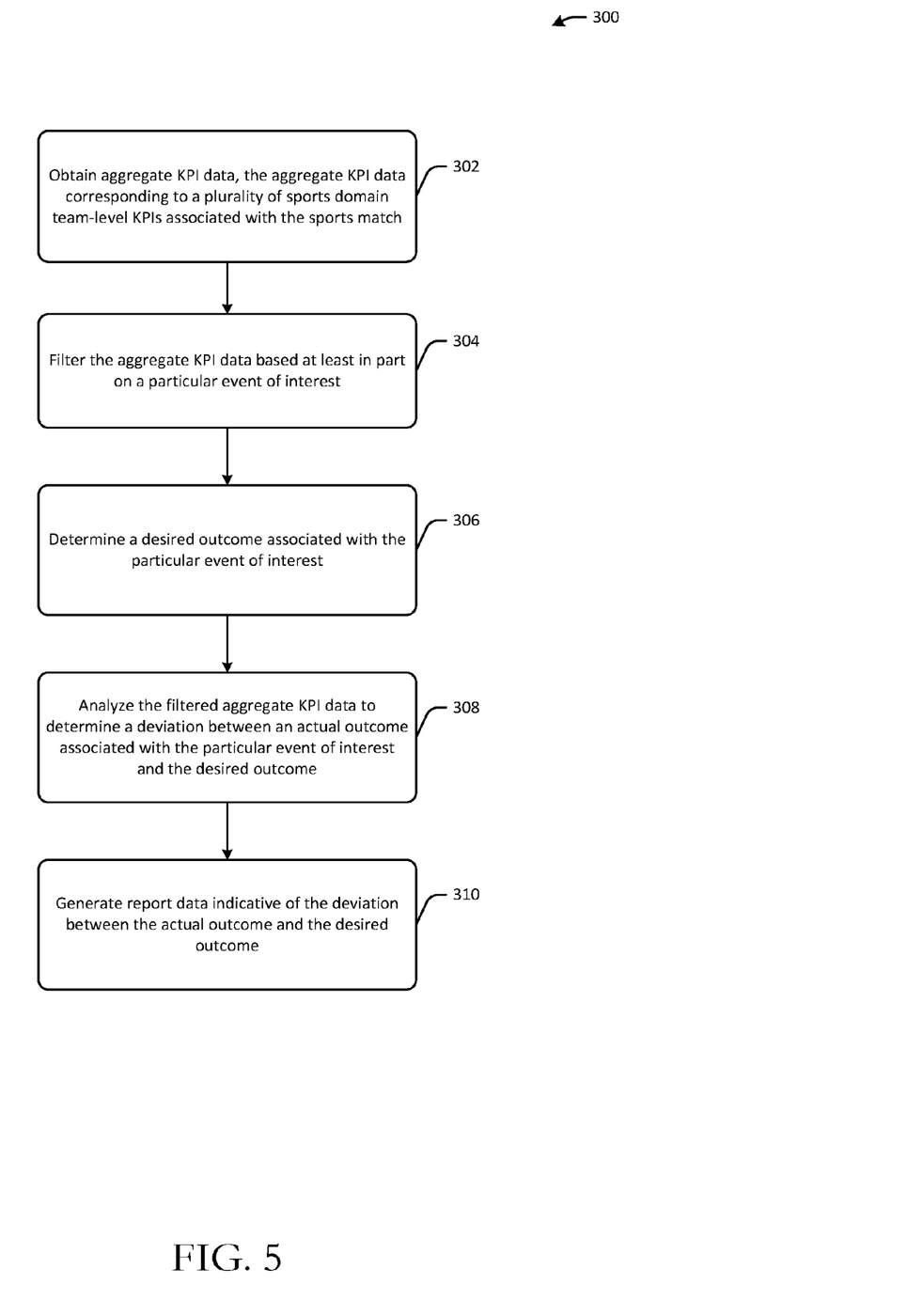
FIG. 5 is a process flow diagram of a method for analyzing aggregate KPI data to determine a deviation between an expected team interaction outcome and an actual team interaction outcome in accordance with one or more example embodiments of the disclosure.

FIG. 3 is a schematic block diagram depicting illustrative components of a three-dimensional (3D) gaze-based team analysis system in accordance with one or more example embodiments of the disclosure. FIG. 4 is a process flow diagram of a method 200 for generating key performance indicator (KPI) data associated with a sports domain KPI based at least in part on gaze parameter data and generating a graph based at least in part on the KPI data indicative of various interactions between team members in accordance with one or more example embodiments of the disclosure. FIG. 5 is a process flow diagram of a method 300 for analyzing aggregate KPI data to determine a deviation between an expected team interaction outcome and an actual team interaction outcome in accordance with one or more example embodiments of the disclosure. FIG. 3 will be described in conjunction with FIG. 4 and FIG. 5 hereinafter.

One or more operations of the methods 200 and 300 may be performed by one or more engines, or more specifically, by one or more program modules or sub-modules forming part of such engine(s). A module, which may contain or be a collection of one or more sub-modules, may include computer-executable instructions that when executed by a processing circuit may cause one or more operations to be performed. A processing circuit may include one or more processing units or nodes. Computer-executable instructions may include computer-executable program code that when executed by a processing unit may cause input data contained in or referenced by the computer-executable program code to be accessed and processed to yield output data. Any module described herein may be implemented in any combination of software, hardware, and/or firmware. Depending on the implementation, any module described herein may form part of a larger collection of modules that together may constitute an engine, an application, or the like.

Referring first to FIG. 3, a 3D gaze-based team analysis system in accordance with one or more example embodiments of the disclosure may include an eye gaze tracking engine 104, a sports match tracking and analysis engine 106, a team analysis engine 108, and a sports domain rules/sports KPI loading engine 110. Each such engine may include computer-executable instructions configured to perform one or more corresponding operations responsive to execution by a processing circuit.

The eye gaze tracking engine 104 may include one or more 3D gaze tracking module(s) 112 which, in turn, may include one or more gaze direction determination module(s) 114, one or more fixation duration determination module(s) 116, and one or more distance determination module(s) 118. The 3D gaze tracking module(s) 112 may be configured to monitor various gaze parameters associated with each member 102(1)-102(N) of a team 102 competing in a sports match. Any given team member will be generically referred to hereinafter as team member 102(X), player 102(X), or the like. The sports match may be any suitable team-based game or match in which two opposing teams compete, each team including a plurality of players (e.g., a soccer match, a doubles tennis match, a baseball game, a cricket match, a basketball game, a golf match, a football game, etc.)

Referring now to FIGS. 3 and 5 in conjunction with one another, at block 202, the 3D gaze tracking module(s) 112 may be executed to monitor over time a respective gaze of each member 102(X) of the team 102 to generate gaze data. More specifically, at block 202, the 3D gaze tracking module(s) 112 may monitor various gaze parameters associated with each team member 102(X) during the sports match and generate gaze parameter data 120 continuously or at periodic intervals of a specified periodicity. The gaze parameter data 120 may include, for example, gaze direction data, gaze fixation duration data, and gaze distance data. The gaze parameter data 120 may be stored in a gaze parameter data repository 122.

For instance, the gaze direction determination module(s) 114 may be executed to monitor a gaze direction of each team member 102(X) to generate the gaze direction data, which may indicate how the direction of each team member's 102(X) gaze changes over time. This may be achieved using a camera that captures images of each team member's 102(X) head over time at a particular frame rate. For each image frame, the gaze direction determination module(s) 114 may determine the angle of each team member's 102(X) head with respect to the camera, and may further determine, for each team member 102(X), the position of the team member's 102(X) eyes with respect to the team member's 102(X) head. The gaze direction determination module(s) 114 may then perform this determination repeatedly across all image frames to determine a scan path that indicates how the direction of each team member's 102(X) gaze changes over time.

The fixation duration determination module(s) 116 may be executed to determine a respective duration of time that each team member's 102 gaze remains in each particular gaze direction. The fixation duration determination module(s) 116 may output gaze fixation duration data that includes a respective series of time durations for each team member 102(X), where each time duration represents an amount of time that a team member's 102 gaze remains in a particular gaze direction.

The distance determination module(s) 118 may be executed to determine distances between points of gaze of each team member 102(X) and objects of interest. Depending on the particular sports domain KPI that is being evaluated, an object of interest may be an object that is exchanged between players during a sports match (e.g., a ball, a puck, etc.), an object that is used by a player to contact the object being exchanged (e.g., a bat, a racket, etc.), a player participating in the sports match, or the like. For example, in the tennis sports domain (e.g., a doubles tennis match), an object of interest for a particular team member 102(1) for a given gaze direction may be the ball, a racket, an opponent, or another team member (e.g., team member 102(2)). The distance determination module(s) 118 may determine a three-dimensional distance between each team member 102(X) and each of one or more objects of interest for each gaze direction and may generate gaze distance data indicative thereof.

As previously noted, the 3D gaze-based team analysis system may include a team analysis engine 108 that may include computer-executable instructions that when executed by a processing circuit may cause operations to be performed to generate an analysis model for interpreting the gaze parameter data 120 within a sports domain by translating a location/time series 124 of the gaze parameter data 120 into KPI data 146 associated with team-level KPIs 144 that are relevant to the sports domain. More specifically, the team analysis engine 108 may include one or more gaze to sports domain KPI mapping modules 130 (hereinafter "mapping module(s) 130)") that may include computer-executable instructions that when executed by a processing circuit may determine gaze-based KPIs from the location/time series gaze parameter data 124 and translate the gaze-based KPIs into KPI data 144 that is relevant to a particular sports domain. The gaze-based KPIs may include, for example, any of the gaze parameters previously described including, but not limited to, a team member's 102(X) gaze direction, a team member's 102(X) gaze duration for a gaze direction, a distance between a team member 102(X) and an object of interest for a particular gaze direction, etc.

Each sports domain may define a plurality of different sports domain team-level KPIs 144 and associated sports domain rules 142. The KPIs 144 and associated domain rules 142 may be loaded into a repository 148 by the sports domain rules/sports KPI loading engine 110, and retrieved therefrom by mapping module(s) 130. Each sports domain may correspond to a particular type of sport, and the mapping module(s) 130 may be configured to translate gaze KPIs into that sports domain's team-level KPIs 144. Each team-level KPI 144 for a given sports domain may be a particular type of team-level performance indicator. In addition, each sports domain team-level KPI 144 may be associated with a set of one or more sports domain rules 142 that define condition(s) based on which the gaze parameter data 120 may be filtered to obtain location/time series gaze parameter data 124 that satisfies the sports domain rule(s) 142. It should be appreciated that, in certain example embodiments, the KPIs 144 may include, in addition to team-level KPIs, one or more KPIs that relate to an individual participant or to a group of participants associated with a same or similar position in a sports domain.

Certain team-level KPIs 144 may be more commonly (or only) applicable to sports matches in which the competing teams include greater than two team members (e.g., a basketball game), while other team-level KPIs 144 may be more commonly (or only) applicable to sports matches in which the competing teams include 2 team members each (e.g., tennis doubles). Team-level KPIs 144 applicable to sports matches involving teams with more than two players may include, without limitation, sub-team mutual gazing; k-cores and k-plexes derived using inter-player gazing; shared attention towards an object of interest under certain conditions; graphs filtered based on gazing behavioral conditions of given players; cross-team chemistry; and so forth. Team-level KPIs 144 applicable to sports matches involving teams having two players each may include, without limitation, mutual gazing; gazing at an object of interest in an scenario in which team members are deciding which team member will take a next action (e.g., player coordination); and so forth.

The above examples of team-level KPIs 144 are generally applicable to multiple different sports domains. In certain example embodiments, team-level KPIs 144 may be defined that are specific to a particular sports domain. For example, a sports domain-specific team-level KPI 144 may be defined as being associated with a particular event or set of events that are only relevant to a particular sports domain, with a team strategy that is only relevant to a particular sports domain, with a set of required criteria that only occur within a particular sports domain, and so forth. As a non-limiting example, a team-level KPI 144 that is specific to the soccer domain may be defined as follows: within 20 yards of the opponent's goal, at least 3 players forming part of the midfield or attack (but not the defense) must be gazing at the ball from a distance that satisfies a threshold distance for at least a threshold period of time.

In addition to accessing the repository 148 to obtain the team-level KPIs 144 and associated sports domain rules 142, the team analysis engine 108 may also receive sports match data 126 as input from the sports match tracking and analysis engine 106. More specifically, the sports match data 126 may be input to the sports match tracking and analysis engine 106 via a user interface 128, and the engine 106 may provide the data 126 as input to the team analysis engine 108. The sports match data 126 may include data indicative of a time of a sports match, a location of the sports match, environmental conditions present at the location of the sports match (e.g., temperature, precipitation, wind speed, etc.). The sports match data 126 may be used by the team analysis engine 108 to determine, for example, how the team-level sports KPIs 144 for the team 102 are impacted by different sports match locations, different times of day at which the sports matches take place, and/or different environmental conditions in which the sports matches occur.

The process performed by the mapping module(s) 130 for translating the location/time series gaze parameter data 124 into KPI data 144 associated with team-level KPIs 144 that are relevant to a sports domain will be described hereinafter in reference to a particular team (e.g., the team 102) and a particular sports domain KPI 144 associated with a particular sports domain. It should be appreciated, however, that the process may be performed for any number of teams (or sub-teams of two or more players) and any number of KPIs 144 associated with any number of sports domains.

Referring again to FIGS. 3 and 5 in conjunction with one another, at block 204, computer-executable instructions of the mapping module(s) 130 may be executed to identify a sports domain team-level KPI 144 associated with a sports domain to which the sports match corresponds. The team-level KPI 144 identified at block 204 may include, any of the example types of team-level KPIs 144 described earlier. In an example embodiment relating to the soccer sports domain, the team-level KPI 144 may be a mutual gazing KPI relating to particular event that may occur within the soccer sports domain such as, for example, an indirect free kick miss near an opponent team's goal. As such, in this context, the mutual gazing KPI 144 may assess the extent to the gaze direction of two or more team members 102(X) coincide (mutual gazing) with respect to the event of an free kick miss near an opponent team's goal.

At block 206, the mapping module(s) 130 may identify one or more sports domain rules 142 associated with the team-level KPI 144 identified at block 204. The sports domain rule(s) 142 may include one or more conditions that the gaze parameter data 120 must satisfy in order to eligible for translation into the KPI data 146 corresponding to the team-level KPI 144 for that sports domain. For instance, for the example team-level KPI 144 relating to an indirect free kick miss near an opponent team's goal, the associated sports domain rule(s) 142 may include a condition that a circular region centered at the location of the free kick and having a diameter of 20 yards be monitored for a monitoring period that begins 5 seconds before the free kick is taken and that ends 5 seconds after the free kick is taken. Monitoring a particular physical region may include monitoring the region to determine whether a player's gaze direction coincides with the monitored region (regardless of whether the player is present in the monitored region) and/or players present in the monitored region during the monitoring period regardless of the direction of their gazing behavior.

At block 208, the mapping module(s) 130 may determine location/time series gaze parameter data 124 that satisfies the sports domain rule(s) 142 identified at block 206. For example, the location/time series gaze parameter data 124 that satisfies the example sports domain rule 142 introduced above may include the gaze direction data, gaze duration data, and gaze distance data for each team member 102(X) whose gaze direction coincides with the monitored region around the location of the free kick during the monitoring period.

At block 210, the mapping module(s) 130 may translate the location/time series gaze parameter data 124 determined to satisfy the sports domain rule(s) 142 into the KPI data 146 associated with the team-level KPI 144 identified at block 206. Referring again to the example introduced earlier, translating the location/time series parameter data 124 into the KPI data 146 may include, for example, determining, based at least in part on the location/time series gaze parameter data 124, that respective gaze parameter data associated with a midfielder (a player who typically occupies a middle section of a playing field) who made an errant pass as part of the free kick scenario indicates that the midfielder's gaze direction failed to coincide with the position of any striker (a player typically positioned closer to the opponent's goal) within the portion of the monitoring period that occurred prior to the free kick attempt.

At block 212, computer-executable instructions of the team graph constructor 132 may be executed by a processing circuit to construct, based at least in part on an analysis of the KPI data 146, a graph indicative of player-object of interest, player-pair, and sub-team interactions associated with the team-level KPI 144. The graph may include a plurality of nodes, where each node may represent a team member 102(X) or a non-player object of interest (e.g., a ball, a bat, etc.), and where edges connecting adjacent nodes may be weighted to indicate the extent of interaction (e.g., mutual gazing) between the entities represented by the connected nodes. For example, a first node in the graph may represent a first team member (e.g., 102(1)) and a second node in the graph may represent a second team member (e.g., 102(2)). The edge connecting the first and second nodes may have an associated weight that indicates, for example, one or more of the following: (i) the degree of overlap between respective gaze vectors for the first and second team members, (ii) the amount or percentage of time within a monitoring period that the respective gaze vectors for the first and second team members overlap by more than a threshold amount of overlap, or the like. The constructed graph may be stored in a data repository 150.

Once the graph is constructed, computer-executable instructions of the team/sub-team/player current activity analysis module(s) 134 may be executed to analyze the graph to determine activity patterns at a team, sub-team, or individual player level. Taking the sports domain of basketball as an example, the graph may be analyzed by the current activity analysis module(s) 134 to determine how different sub-team make-ups perform for a team-level sports KPI 144 (e.g. a pick-and-roll situation). For example, analysis of the graph may reveal that team member 102(3) more frequently moves to the appropriate spot on the court after rolling off a pick-and-roll with team member 102(1) than does team member 102(2); that team members 102(1) and 102(3) have more overlap in their mutual gazing behavior than team members 102(1) and 102(2) during pick-and-roll situations; or the like.

FIG. 5 details an example method 300 according to which KPI data 146 aggregated over multiple team-level sports KPIs 144 is filtered for a particular event of interest to determine how an actual response of the team 102 to the event interest deviated from an expected response. Referring now to FIGS. 3 and 5 in conjunction with one another, at block 302, one or more aggregate activity analysis modules 136 may be executed by a processing circuit to obtain aggregate KPI data, the aggregate KPI data corresponding to a plurality of team-level KPIs associated with a particular sports match. Using the soccer sports domain as an example, the aggregate KPI data may correspond to reaction/response times, focus/attentiveness metrics, etc. for different events that may occur during a sports match within that sports domain (e.g. a counterattack, a free kick, a corner kick, etc.).

At block 304, computer-executable instructions of the aggregate activity analysis module(s) 136 may be executed to filter the aggregate KPI data 146 based at least in part on a particular event of interest. Referring again to soccer sports domain example introduced earlier, the particular event of interest may be an indirect free kick miss near an opponent's goal.

At block 306, computer-executable instructions of one or more sync analysis modules 138 may be executed to determine a desired outcome associated with the particular event of interest. Then, at block 308, computer-executable instructions of the sync analysis module(s) 138 may be executed to determine factors that may have caused a deviation between the actual outcome and the desired outcome.

For example, if the particular event of interest is an indirect free kick miss near an opponent's goal, the desired outcome may be a scored goal, or at a minimum, a shot on goal. The analysis of the filtered aggregate KPI data, however, may reveal that the gazing behavior of 2 of 6 players with a relevant physical region did not gaze at the ball within a monitoring period that both preceded and came after the moment the free kick was taken. The analysis of the filtered aggregate KPI data 146 may further reveal that the player taking the free kick did not gaze at the goalie during a threshold amount of time prior to taking the free kick. Thus, the analysis performed at block 308 may reveal factors (e.g., mutual gazing behavior, player gazing behavior towards an object of interest, etc.) that may be indicative of a lack of team chemistry that may, in turn, have caused the actual outcome for the event of interest to deviate from the desired outcome for the event of interest.

Based on the analysis of the filtered aggregate KPI data performed at block 308, computer-executable instructions of the report generation module(s) 140 may be executed to generate report data indicative of the factors that may have caused the deviation between the actual outcome and the desired outcome. For example, the report data may indicate gazing behavior among members of the team 102 that may have contributed to a diminished team synchronization that, in turn, may have led to the actual outcome (e.g., missed free kick) deviating from the expected outcome (e.g., shot on goal).

One or more illustrative embodiments of the disclosure are described herein. Such embodiments are merely illustrative of the scope of this disclosure and are not intended to be limiting in any way. Accordingly, variations, modifications, and equivalents of embodiments disclosed herein are also within the scope of this disclosure.

Figure 6:
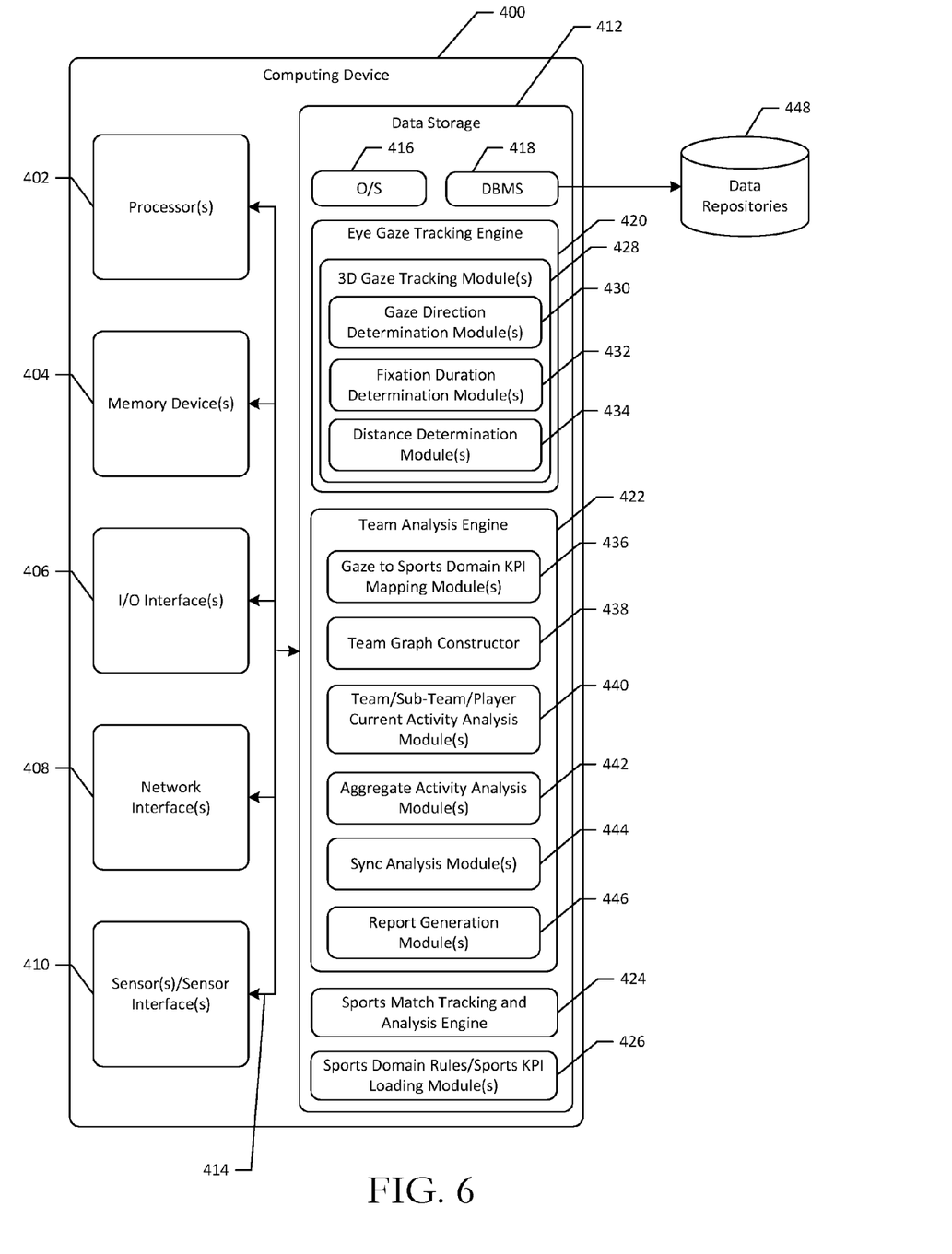
FIG. 6 is a schematic diagram of an illustrative computing device that is configured to implementation processes in accordance with one or more example embodiments of the disclosure.

FIG. 6 is a schematic diagram of an illustrative computing device 400 that is configured to implement processes in accordance with one or more example embodiments of the disclosure in accordance with one or more example embodiments of the disclosure. While the computing device 400 may be described herein in the singular, it should be appreciated that multiple instances of the computing device 400 may be provided, and functionality described in connection with the computing device 400 may be distributed across such multiple instances.

In an illustrative configuration, the computing device 400 may include one or more processors (processor(s)) 402, one or more memory devices 404 (generically referred to herein as memory 404), one or more input/output ("I/O") interface(s) 406, one or more network interfaces 408, one or more sensors or sensor interface(s) 410, and data storage 412. The computing device 400 may further include one or more buses 414 that functionally couple various components of the computing device 400.

The bus(es) 414 may include at least one of a system bus, a memory bus, an address bus, or a message bus, and may permit exchange of information (e.g., data (including computer-executable code), signaling, etc.) between various components of the computing device 800. The bus(es) 414 may include, without limitation, a memory bus or a memory controller, a peripheral bus, an accelerated graphics port, and so forth. The bus(es) 414 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 404 of the computing device 400 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 404 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 404 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 412 may include removable storage and/or non-removable storage including, but not limited to, magnetic storage, optical disk storage, and/or tape storage. The data storage 412 may provide non-volatile storage of computer-executable instructions and other data. The memory 404 and the data storage 412, removable and/or non-removable, are examples of computer-readable storage media (CRSM) as that term is used herein.

The data storage 412 may store computer-executable code, instructions, or the like that may be loadable into the memory 404 and executable by the processor(s) 402 to cause the processor(s) 402 to perform or initiate various operations. The data storage 412 may additionally store data that may be copied to memory 404 for use by the processor(s) 402 during the execution of the computer-executable instructions. Moreover, output data generated as a result of execution of the computer-executable instructions by the processor(s) 402 may be stored initially in memory 404 and may ultimately be copied to data storage 412 for non-volatile storage.

More specifically, the data storage 412 may store one or more operating systems (O/S) 416; one or more database management systems (DBMS) 418 configured to access the memory 404 and/or one or more external data repositories 448; and one or more program modules, applications, engines, computer-executable code, scripts, or the like such as, for example, an eye gaze tracking engine 420, a team analysis engine 422, a sports match tracking and analysis engine 424, and a sports domain rules/sports KPI loading engine 426. The eye gaze tracking engine 420 may include one or more 3D gaze tracking modules 428, which in turn, may include one or more sub-modules such as, for example, one or more gaze direction determination modules 430, one or more fixation determination duration modules 432, and one or more distance determination modules. The team analysis engine 422 may further include gaze to sports domain KPI mapping modules 436, a team graph constructor 438, one or more team/sub-team/player current activity analysis modules 440, one or more aggregate activity analysis modules 442, one or more sync analysis modules 444, and one or more report generation modules 446. Any of the components depicted as being stored in data storage 412 may include any combination of software, firmware, and/or hardware. The software and/or firmware may include computer-executable instructions (e.g., computer-executable program code) that may be loaded into the memory 404 for execution by one or more of the processor(s) 402 to perform any of the operations described earlier in connection with correspondingly named engines or modules.

Although not depicted in FIG. 6, the data storage 412 may further store various types of data utilized by components of the computing device 400 (e.g., the gaze parameter data 120, data indicative of sports domain rules 142, data indicative of team-level sports KPIs 144, KPI data 146, sports match data 126, etc.). Any data stored in the data storage 412 may be loaded into the memory 404 for use by the processor(s) 402 in executing computer-executable instructions. In addition, any data stored in the data storage 412 may potentially be stored in one or more of the data repositories 444 and may be accessed via the DBMS 418 and loaded in the memory 404 for use by the processor(s) 402 in executing computer-executable instructions.

The processor(s) 402 may be configured to access the memory 404 and execute computer-executable instructions loaded therein. For example, the processor(s) 402 may be configured to execute computer-executable instructions of the various program modules, applications, engines, or the like of the computing device 400 to cause or facilitate various operations to be performed in accordance with one or more embodiments of the disclosure. The processor(s) 402 may include any suitable processing unit capable of accepting data as input, processing the input data in accordance with stored computer-executable instructions, and generating output data. The processor(s) 402 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 402 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 402 may be capable of supporting any of a variety of instruction sets.

Referring now to other illustrative components depicted as being stored in the data storage 412, the O/S 416 may be loaded from the data storage 412 into the memory 404 and may provide an interface between other application software executing on the computing device 400 and hardware resources of the computing device 400. More specifically, the O/S 416 may include a set of computer-executable instructions for managing hardware resources of the computing device 400 and for providing common services to other application programs (e.g., managing memory allocation among various application programs). In certain example embodiments, the O/S 416 may control execution of one or more of the program modules depicted as being stored in the data storage 412. The O/S 416 may include any operating system now known or which may be developed in the future including, but not limited to, any server operating system, any mainframe operating system, or any other proprietary or non-proprietary operating system.

The DBMS 418 may be loaded into the memory 404 and may support functionality for accessing, retrieving, storing, and/or manipulating data stored in the memory 404, data stored in the data storage 412, and/or data stored in the data repositories 448. The DBMS 418 may use any of a variety of database models (e.g., relational model, object model, etc.) and may support any of a variety of query languages. The DBMS 418 may access data represented in one or more data schemas and stored in any suitable data repository. The data repositories 448 may be accessible by the computing device 400 via the DBMS 418 may include, but are not limited to, databases (e.g., relational, object-oriented, etc.), file systems, flat files, distributed datastores in which data is stored on more than one node of a computer network, peer-to-peer network datastores, or the like. The data repositories 448 may include the repository 122, the repository 148, and the repository 150, and may store various types of data including, without limitation, the gaze parameter data 120, data indicative of sports domain rules 142, data indicative of team-level sports KPIs 144, KPI data 146, sports match data 126, etc. It should be appreciated that, in certain example embodiments, any of the data repositories 448 and/or any of the data residing thereon may additionally, or alternatively, be stored locally in the data storage 412.

Referring now to other illustrative components of the computing device 400, the input/output (I/O) interface(s) 406 may facilitate the receipt of input information by the computing device 400 from one or more I/O devices as well as the output of information from the computing device 400 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the computing device 400 or may be separate. The I/O devices may further include, for example, any number of peripheral devices such as data storage devices, printing devices, and so forth.

The I/O interface(s) 406 may also include an interface for an external peripheral device connection such as universal serial bus (USB), FireWire, Thunderbolt, Ethernet port or other connection protocol that may connect to one or more networks. The I/O interface(s) 406 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The computing device 400 may further include one or more network interfaces 408 via which the computing device 400 may communicate with any of a variety of other systems, platforms, networks, devices, and so forth. The network interface(s) 408 may enable communication, for example, with one or more other devices via one or more networks. Such network(s) may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

The sensor(s)/sensor interface(s) 410 may include or may be capable of interfacing with any suitable type of sensing device such as, for example, ambient light sensors, inertial sensors, force sensors, thermal sensors, image sensors, magnetometers, and so forth. Example types of inertial sensors may include accelerometers (e.g., MEMS-based accelerometers), gyroscopes, and so forth.

It should be appreciated that the engines and program modules depicted in FIG. 6 as being stored in the data storage 412 are merely illustrative and not exhaustive and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the computing device 400 and/or hosted on other computing device(s) accessible via one or more networks, may be provided to support functionality provided by the engines or modules depicted in FIG. 6 and/or additional or alternate functionality. Further, functionality may be modularized differently such that processing described as being supported collectively by a collection of modules depicted in FIG. 6 may be performed by a fewer or greater number of program modules, or functionality described as being supported by any particular module may be supported, at least in part, by another program module. In addition, engines or program modules that support the functionality described herein may form part of one or more applications executable across any number of computing devices 400 in accordance with any suitable computing model such as, for example, a client-server model, a peer-to-peer model, and so forth. In addition, any of the functionality described as being supported by any of the engines or program modules depicted in FIG. 6 may be implemented, at least partially, in hardware and/or firmware across any number of devices.

It should further be appreciated that the computing device 400 may include alternate and/or additional hardware, software, or firmware components beyond those described or depicted without departing from the scope of the disclosure. More particularly, it should be appreciated that software, firmware, or hardware components depicted as forming part of the computing device 400 are merely illustrative and that some components may not be present or additional components may be provided in various embodiments. While various illustrative engines and program modules have been depicted and described as software modules stored in data storage 412, it should be appreciated that functionality described as being supported by the engines or modules may be enabled by any combination of hardware, software, and/or firmware. It should further be appreciated that each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain modules may be depicted or described as sub-modules of another module, in certain embodiments, such modules may be provided as independent modules or as sub-modules of other modules.

One or more operations of the methods 200 and 300 may be performed by a computing device 400 having the illustrative configuration depicted in FIG. 6, or more specifically, by one or more program modules, engines, applications, or the like executable on such a device. It should be appreciated, however, that such operations may be implemented in connection with numerous other device configurations.

The operations described and depicted in the illustrative methods of FIGS. 4 and 5 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 4 and 5 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure. In addition, it should be appreciated that any operation, element, component, data, or the like described herein as being based on another operation, element, component, data, or the like may be additionally based on one or more other operations, elements, components, data, or the like. Accordingly, the phrase "based on," or variants thereof, should be interpreted as "based at least in part on."

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for analyzing interactions between members of a team using gaze parameter data, the method comprising:
    capturing, by an image sensor over a period of time during a sports match, the gaze parameter data, wherein the gaze parameter data comprises first gaze parameter data associated with a first member of the team and second gaze parameter data associated with a second member of the team, and wherein capturing the first gaze parameter data comprises:
        capturing, at a particular frame rate, a series of image frames of a head of the first member;
        determining, for each image frame, an angle between the head of the first member and the image sensor;
        determining, for each image frame, an eye position of the first member; and
        determining a scan path based at least in part on the angle between the head of the first member and the image sensor determined for each image frame and the eye position of the first member determined for each image frame, wherein the scan path indicates a change in gaze direction of the first member over a time period during which the series of image frames are captured;
    identifying, by a computer processor, a sports domain associated with the sports match;
    identifying, by the computer processor, a key performance indicator (KPI) corresponding to the sports domain;
    identifying, by the computer processor, one or more sports domain rules associated with the KPI;
    filtering, by the computer processor, the gaze parameter data to obtain a location/time series of the gaze parameter data that satisfies the one or more sports domain rules;
    generating, by the computer processor, KPI data associated with the KPI based at least in part on the location/time series of the gaze parameter data; and
    analyzing, by the computer processor, the KPI data to determine a mutual gazing behavior between the first member of the team and the second member of the team.

2. The computer-implemented method of claim 1, further comprising:
    constructing, by the computer processor, a graph based at least in part on analyzing the KPI data, wherein the graph comprises a first node representing the first member of the team and a second node representing the second member of the team, and wherein an edge connecting the first node and the second node is representative of the mutual gazing behavior.

3. The computer-implemented method of claim 2, wherein constructing the graph comprises determining a weight of the edge connecting the first node and the second node based at least in part on at least one of an amount of overlap or a duration of overlap between a first gaze direction associated with the first member of the team and a second gaze direction associated with the second member of the team during a monitoring period associated with the KPI.

4. The computer-implemented method of claim 1, wherein the KPI corresponds to a type of event that occurs during the sports match, wherein the one or more sports domain rules comprises a rule specifying a predetermined period of time prior to the occurrence of the event that the member of the team are to be monitored, and wherein filtering the gaze parameter data comprises determining that the location/time series of the gaze parameter data was captured during the predetermined period of time.

5. The computer-implemented method of claim 4, where the rule further specifies that the participant is to be monitored within a predetermined physical region encompassing a physical location of the event, and wherein filtering the gaze parameter data further comprises determining that the location/time series of the gaze parameter data was captured while each of the members of the team was located within the predetermined physical region during the predetermined period of time or was associated with a gazing direction that coincided with the predetermined physical region during the predetermined period of time.

6. The computer-implemented method of claim 1, wherein the KPI data is first KPI data and the KPI is a first KPI, the method further comprising:
    aggregating, by the computer processor, the first KPI data with second KPI data corresponding to a second KPI to obtain aggregate KPI data;
    filtering, by the computer processor, the aggregate KPI data based at least in part on an event of interest during the sports match to obtain filtered aggregate KPI data;
    determining, by the computer processor, a desired outcome associated with the event of interest; and
    analyzing, by the computer processor, the filtered aggregate KPI data to determine one or more team synchronization events causing a deviation between an actual outcome associated with the event of interest and the desired outcome.

7. The computer-implemented method of claim 6, further comprising:
generating, by the computer processor, report data indicative of the one or more team synchronization events; and
presenting, by the computer processor, the report data to the members of the team during the sports match.

8. A system for analyzing interactions between members of a team using gaze parameter data, the system comprising:
at least one memory storing computer-executable instructions; and
at least one processor configured to access the at least one memory and execute the computer-executable instructions to:
capture, via an image sensor over a period of time during a sports match, the gaze parameter data, wherein the gaze parameter data comprises first gaze parameter data associated with a first member of the team and second gaze parameter data associated with second member of the team, and wherein the at least one processor is configured to capture the first gaze parameter data by:
capturing, at a particular frame rate, a series of image frames of a head of the first member;
determining, for each image frame, an angle between the head of the first member and the image sensor;
determining, for each image frame, an eye position of the first member; and
determining a scan path based at least in part on the angle between the head of the first member and the image sensor determined for each image frame and the eye position of the first member determined for each image frame, wherein the scan path indicates a change in gaze direction of the first member over a time period during which the series of image frames are captured;
identify a sports domain associated with the sports match;
identify a key performance indicator (KPI) corresponding to the sports domain;
identify one or more sports domain rules associated with the KPI;
filter the gaze parameter data to obtain a location/time series of the gaze parameter data that satisfies the one or more sports domain rules;
generate KPI data associated with the KPI based at least in part on the location/time series of the gaze parameter data; and
analyze the KPI data to determine a mutual gazing behavior between the first member of the team and the second member of the team.

9. The system of claim 8, wherein the at least one processor is further configured to execute the computer-executable instructions to:
construct a graph based at least in part on analyzing the KPI data, wherein the graph comprises a first node representing the first member of the team and a second node representing the second member of the team, and wherein an edge connecting the first node and the second node is representative of the mutual gazing behavior.

10. The system of claim 9, wherein the at least one processor is configured to construct the graph by executing the computer-executable instructions to determine a weight of the edge connecting the first node and the second node based at least in part on at least one of an amount of overlap or a duration of overlap between a first gaze direction associated with the first member of the team and a second gaze direction associated with the second member of the team during a monitoring period associated with the KPI.

11. The system of claim 8, wherein the KPI corresponds to a type of event that occurs during the sports match, wherein the one or more sports domain rules comprises a rule specifying a predetermined period of time prior to the occurrence of the event that the member of the team are to be monitored, and wherein the at least one processor is configured to filter the gaze parameter data by executing the computer-executable instructions to determine that the location/time series of the gaze parameter data was captured during the predetermined period of time.

12. The system of claim 11, where the rule further specifies that the participant is to be monitored within a predetermined physical region encompassing a physical location of the event, and wherein the at least one processor is configured to filter the gaze parameter data by executing the computer-executable instructions to determine that the location/time series of the gaze parameter data was captured while each of the members of the team was located within the predetermined physical region during the predetermined period of time or was associated with a gazing direction that coincided with the predetermined physical region during the predetermined period of time.

13. The system of claim 8, wherein the KPI data is first KPI data and the KPI is a first KPI, and wherein the at least one processor is further configured to execute the computer-executable instructions to:
aggregate the first KPI data with second KPI data corresponding to a second KPI to obtain aggregate KPI data;
filter the aggregate KPI data based at least in part on an event of interest during the sports match to obtain filtered aggregate KPI data;
determine a desired outcome associated with the event of interest; and
analyze the filtered aggregate KPI data to determine one or more team synchronization events causing a deviation between an actual outcome associated with the event of interest and the desired outcome.

14. The system of claim 13, wherein the at least one processor is further configured to execute the computer-executable instructions to:
generate report data indicative of the one or more team synchronization events; and
present the report data to the members of the team during the sports match.

15. A computer program product for analyzing interactions between members of a team using gaze parameter data, the computer program product comprising a non-transitory storage medium readable by a processing circuit, the storage medium storing instructions executable by the processing circuit to cause a method to be performed, the method comprising:
obtaining the gaze parameter data, wherein the gaze parameter data is captured by an image sensor over a period of time during a sports match, and wherein the gaze parameter data comprises first gaze parameter data associated with a first member of the team and second gaze parameter data associated with second member of the team, and wherein the first gaze parameter data is captured by:
capturing, at a particular frame rate, a series of image frames of a head of the first member;

determining, for each image frame, an angle between the head of the first member and the image sensor;

determining, for each image frame, an eye position of the first member; and determining a scan path based at least in part on the angle between the head of the first member and the image sensor determined for each image frame and the eye position of the first member determined for each image frame, wherein the scan path indicates a change in gaze direction of the first member over a time period during which the series of image frames are captured;

identifying a sports domain associated with the sports match;

identifying, by the computer processor, a key performance indicator (KPI) corresponding to the sports domain;

identifying one or more sports domain rules associated with the KPI;

filtering the gaze parameter data to obtain a location/time series of the gaze parameter data that satisfies the one or more sports domain rules;

generating KPI data associated with the KPI based at least in part on the location/time series of the gaze parameter data; and analyzing the KPI data to determine a mutual gazing behavior between the first member of the team and the second member of the team.

16. The computer program product of claim 15, the method further comprising:

constructing a graph based at least in part on analyzing the KPI data, wherein the graph comprises a first node representing the first member of the team and a second node representing the second member of the team, and wherein an edge connecting the first node and the second node is representative of the mutual gazing behavior.

17. The computer program product of claim 16, wherein constructing the graph comprises determining a weight of the edge connecting the first node and the second node based at least in part on at least one of an amount of overlap or a duration of overlap between a first gaze direction associated with the first member of the team and a second gaze direction associated with the second member of the team during a monitoring period associated with the KPI.

18. The computer program product of claim 15, wherein the KPI corresponds to a type of event that occurs during the sports match, wherein the one or more sports domain rules comprises a rule specifying a predetermined period of time prior to the occurrence of the event that the member of the team are to be monitored, and wherein filtering the gaze parameter data comprises determining that the location/time series of the gaze parameter data was captured during the predetermined period of time.

19. The computer program product of claim 18, where the rule further specifies that the participant is to be monitored within a predetermined physical region encompassing a physical location of the event, and wherein filtering the gaze parameter data further comprises determining that the location/time series of the gaze parameter data was captured while each of the members of the team was located within the predetermined physical region during the predetermined period of time or was associated with a gazing direction that coincided with the predetermined physical region during the predetermined period of time.

20. The computer program product of claim 15, wherein the KPI data is first KPI data and the KPI is a first KPI, the method further comprising:

aggregating the first KPI data with second KPI data corresponding to a second KPI to obtain aggregate KPI data;

filtering the aggregate KPI data based at least in part on an event of interest during the sports match to obtain filtered aggregate KPI data;

determining a desired outcome associated with the event of interest; and analyzing the filtered aggregate KPI data to determine one or more team synchronization events causing a deviation between an actual outcome associated with the event of interest and the desired outcome.

* * * * *